(12) United States Patent
Vandenbroek et al.

(10) Patent No.: US 7,341,145 B2
(45) Date of Patent: Mar. 11, 2008

(54) SINGLE FIRE VASCULAR LIGATION CLIP DISPENSER

(75) Inventors: Frans Vandenbroek, Rancho Santa Margarita, CA (US); Arnold Tuason, Santa Fe Springs, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 474 days.

(21) Appl. No.: 11/124,474

(22) Filed: May 5, 2005

(65) Prior Publication Data
US 2006/0249410 A1 Nov. 9, 2006

(51) Int. Cl.
*B65D 85/08* (2006.01)
(52) U.S. Cl. .................. 206/339; 206/340; 606/157
(58) Field of Classification Search ............ 206/338, 206/339, 340, 341, 348, 438
See application file for complete search history.

(56) References Cited

U.S. PATENT DOCUMENTS

| | | | |
|---|---|---|---|
| 1,575,065 A | 3/1926 | Kingsbury | |
| 3,090,610 A | 5/1963 | Johansson | |
| 3,186,246 A | 6/1965 | Slinker | |
| 3,601,302 A | 8/1971 | Potekhina et al. | |
| 4,344,531 A | 8/1982 | Giersch | |
| 4,448,193 A | 5/1984 | Ivanov | |
| 4,572,403 A | 2/1986 | Benaroya | |
| 4,696,396 A | 9/1987 | Samuels | |
| 4,821,721 A * | 4/1989 | Chin et al. | 606/143 |
| 4,821,878 A | 4/1989 | Jones | |
| 4,936,447 A | 6/1990 | Peiffer | |
| 4,938,353 A | 7/1990 | Bell | |
| 4,961,499 A | 10/1990 | Kulp | |
| 4,971,198 A | 11/1990 | Mericle | |
| 5,032,127 A | 7/1991 | Frazee et al. | |
| 5,199,565 A | 4/1993 | Voroba | |
| 5,478,345 A | 12/1995 | Stone et al. | |
| 5,695,502 A | 12/1997 | Pier et al. | |
| 5,908,430 A | 6/1999 | Appleby | |
| 6,419,682 B1 | 7/2002 | Appleby | |
| 2002/0017472 A1 | 2/2002 | Weisshaupt | |
| 2006/0124485 A1* | 6/2006 | Kennedy | 206/340 |

FOREIGN PATENT DOCUMENTS

| | | |
|---|---|---|
| GB | 1329393 | 9/1973 |
| GB | 2186269 | 8/1987 |

OTHER PUBLICATIONS

MC Carthy, M.D., "An Automatic Spur Serature Clip Dispenser", Surgery, Mar. 1962, pp. 391-392.
European Patent Office, The International Search Report and the Written Opinion for International Application No. PCT/US2006/007235, 10 pages, mailed Jun. 23, 2006.

* cited by examiner

*Primary Examiner*—Jacob K. Ackun, Jr.
(74) *Attorney, Agent, or Firm*—David G. Majdali; Cynthia A. Bonner; Patrick Y. Ikehara

(57) ABSTRACT

A surgical clip dispenser arranged to hold a plurality of surgical clips for retrieval by a clip applier is provided. The dispenser in one aspect includes a clip housing with a plurality of slots each adapted to hold a plurality of surgical clips and is biased for rotational movement. A regulator substantially encompassed by the clip housing in one position prevents rotational movement of the clip housing and in another position permits rotation of the clip housing.

20 Claims, 8 Drawing Sheets

SINGLE FIRE VASCULAR LIGATION CLIP DISPENSER

BACKGROUND

This invention relates generally to surgical clip appliers and surgical clips and, more particularly, to a surgical clip dispenser and methods for retrieving a surgical clip from the surgical clip dispenser.

Endoscopic surgical techniques, including laparoscopic and arthroscopic techniques, are gaining wide acceptance and are being increasingly used. There are many benefits associated with these minimally invasive techniques, which include, reduced patient trauma, reduced risk of post-operative infection and reduced recovery time.

Various types of surgical instruments have been developed for use with these endoscopic surgical techniques and procedures, including clip appliers for the occlusion and ligation of vessels as well as other conduits and tissue structures. Clip appliers typically include a handle connected to a pair of clip compressing jaw members. In one configuration, the jaw members are movable with respect to each other when a user, e.g., a surgeon, operates the handle. A surgical clip loaded in between each jaw member is placed over or around the desired section of tissue, vessel, another clip or another similar object. The clip is compressed as the jaw members move toward each other thereby applying the clip.

However, retrieving a clip to place it in between the jaw members of a clip applier can be a difficult task. As the clips are often small, visually locating a clip by itself or among numerous clips or other objects can prove difficult. Additionally, due to a clip's size and malleable nature, a clip may be dropped, lost, deformed and/or improperly loaded when the clip is handled or retrieved by hand or using a clip applier. Thus, operating ease and ensuring accuracy of clip dispensing and retrieving are desirable.

SUMMARY

The present invention provides a manual and/or automatic surgical clip dispenser and methods thereof. In one aspect of the current invention, a surgical clip dispenser holding and dispensing a plurality of surgical clips for retrieval by a clip applier is provided. The dispenser comprises a clip housing, a spring, and a regulator or actuator, e.g., a button or pawl plate, in one aspect of the present invention. The clip housing, e.g., the carousel, comprises a plurality of walls with consecutive opposed walls defining a slot arranged to hold a surgical clip of the plurality of surgical clips. The spring induces rotational movement on the clip housing. The regulator in one embodiment is substantially encompassed by the clip housing and has at least one projection that is operationally engagable with a portion of the clip housing. The regulator is also movable between a first position preventing movement of the clip housing and a second position permitting movement of the clip housing.

In another embodiment, a surgical clip dispenser comprises holder means, e.g., a carousel, storing a plurality of surgical clips, bias means, e.g., a spiral spring, inducing rotational movement of the holder means and resilient means, e.g., an actuator, permitting the holder means to rotate for a predetermined angular rotation in a first position and for preventing rotational movement of the holder means in a second position.

In a further embodiment, a surgical clip dispenser comprises a carousel having an outer periphery, an inner periphery, and a plurality of walls disposed radially on the carousel with each consecutive opposed wall defining a slot adapted to holding a surgical clip and a plurality of protrusions proximate each wall disposed along the inner periphery. The dispenser also comprises a spiral spring connected to the carousel between the inner periphery and the outer periphery to induce rotational movement, an actuator substantially surrounded by the carousel within the inner periphery of the carousel with at least one tooth extending from a periphery of the actuator operatively engaging at least one of the plurality of protrusions and a spring connected to the actuator. The dispenser further comprises a base connected to the carousel and the spiral spring and a lid connected to the base and including a surface having a window disposed there through and having raised portions extending from the surface of the lid.

Many of the attendant features of the present invention will be more readily appreciated as the same becomes better understood by reference to the following detailed description and considered in connection with the accompanying drawings in which like reference symbols designate like parts throughout.

DETAILED DESCRIPTION

Figure 1:
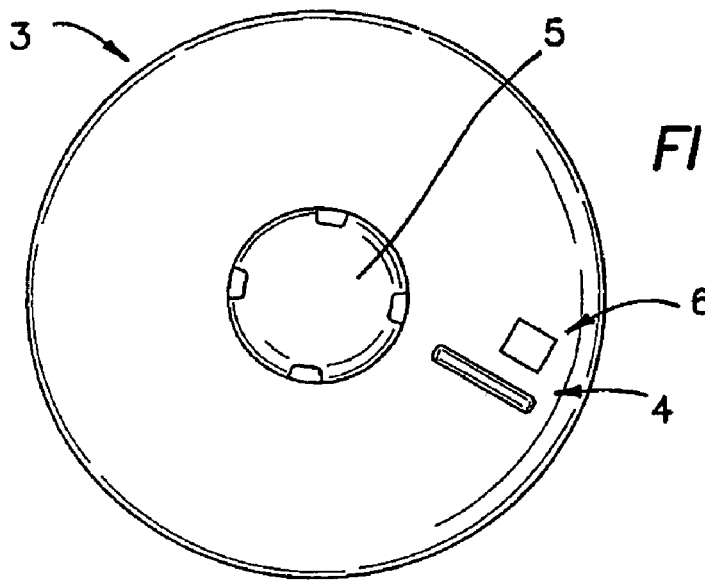
FIG. 1 is a top view of one embodiment of a surgical clip dispenser.

In FIG. 1, one embodiment of a clip dispenser 3 is shown. The clip dispenser 3 houses numerous surgical clips. A surgical clip, in one aspect of the present invention, is generally U-shaped or V-shaped with a pair of outwardly extending and generally opposed legs connected at an apex and twelve to twenty-four clips are stored in the dispenser 3. A single clip is exposed and accessible through clip window 4. Jaw members of a clip applier (not shown) are inserted through the clip window 4, which guides the jaw members to retrieve the exposed clip. After the clip has been retrieved, a button 5 or another type of actuator or regulator is engaged to cause the dispenser 3 to expose another clip. A clip indicator 6 identifies number of clips dispensed or the number of clips remaining in the dispenser. As a result, a user can quickly identify, locate and retrieve a clip from the dispenser 3 and is provided feedback as to the number of clips left in the dispenser and/or the number of clips retrieved.

Figure 2:
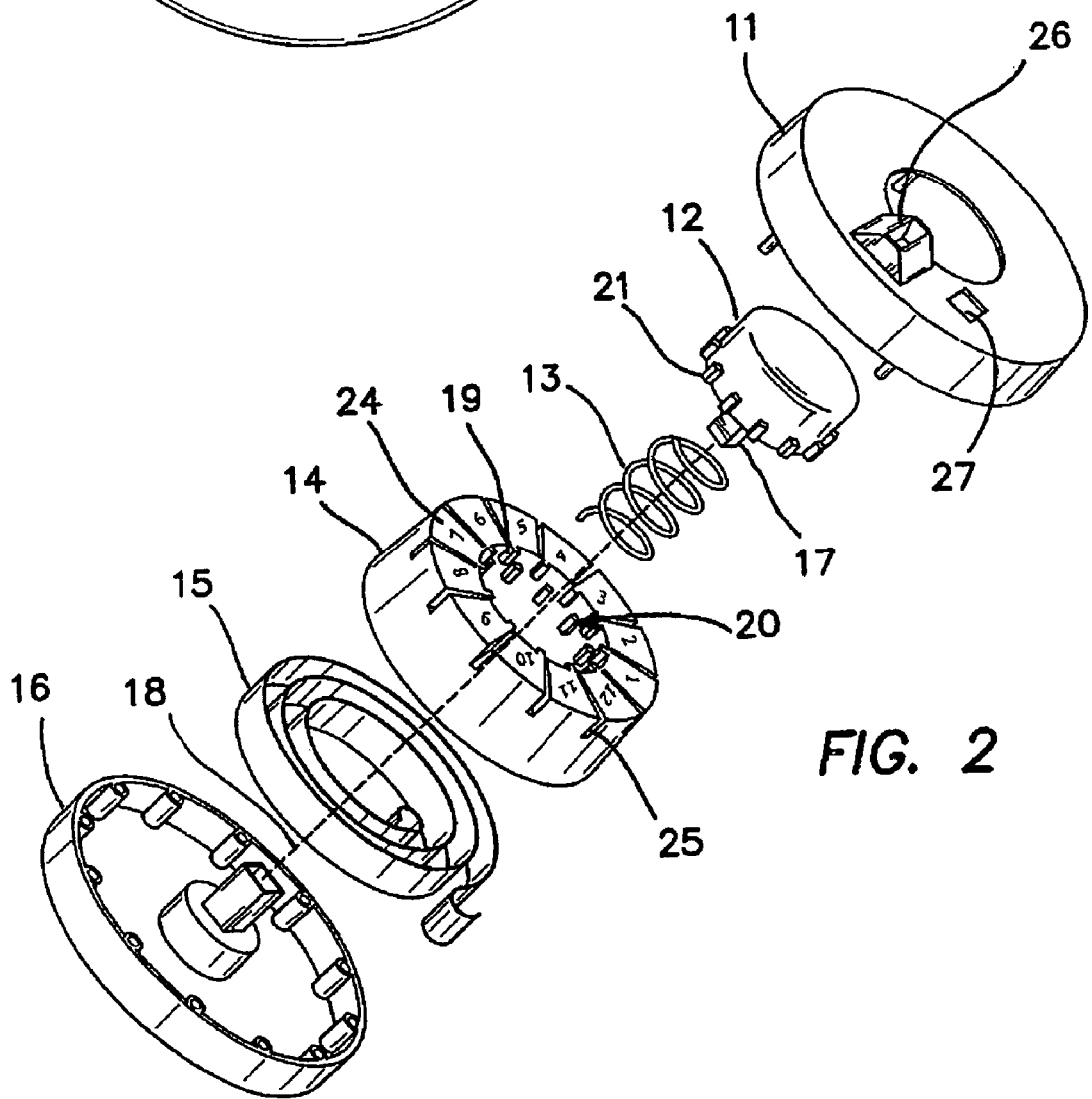
FIG. 2 is an exploded perspective view of one embodiment of a surgical clip dispenser.

Referring now to FIG. 2, one embodiment of a clip dispenser of, for example, FIG. 1 including a lid 11 and a button 12 is shown. The button 12 is slidably connected and extends through an opening in the lid 11. A compression spring 13 is disposed in a cavity of the button or actuator 12. The compression spring 13 contacting a base 16 and substantially surrounding counteracting means, e.g., a square shaft 17, that extends from button 12 assists the button 12 in moving along a dispenser axis 18. When actuated, e.g., depressed, the button 12 travels substantially along the dispenser axis 18 towards the base 16 as the compression spring compresses. Contact of the square shaft 17 with the base 16, in one embodiment, prevents further movement of the button 12 towards the base 16. Compression spring 13 extending returns button 12 back to its original position, e.g., extending partially through the opening in the lid 11, when pressure is removed from button 12. The button 12 and compression spring 13 are also disposed in an opening in a clip housing, e.g., carousel 14.

The lid 11 is connected to base 16 using a snap-fitting engagement, in one embodiment. The lid 11 and base 16 thus define an enclosure or container for the carousel 14, a spiral or coil spring 15 and clips 30 disposed in the carousel 14. The button 12 extends through the opening in lid 11, but teeth 21 radially extending from the button 12 prevents the button from dislodging from lid 11 to retain the button 12 as well as compression spring 13 within the enclosure. In one embodiment, the compression spring 13 is attached on one end to the button 12 and on the other end to base 16 that further secures the button 12 to the enclosure.

In one aspect of the present invention, a corresponding square housing, recess or slot disposed in and extending from a cavity formed in base 16 receives the square shaft 17 for a piston-type arrangement. The interaction of the square housing with the square shaft counteracts the rotational force applied by the spiral spring 15 through the carousel 14 to prevent or restrict rotational movement of button 12. The square or cornered shaft 17, however, extends and slides within the square housing, e.g., counteracting means, such that the button 12 travels along the dispenser axis 18. The compression spring 13 winds around the square shaft 17 and the square housing and rests on base 16. In one aspect of the present invention, the compression spring 13 is disposed within the square shaft 17 and/or the square housing.

Carousel 14 includes numerous slots disposed radially on the carousel 14. Twelve slots are shown in FIG. 2, though more or less slots may be provided. Initially and for most applications, a surgical clip is placed in each of the slots 25. In one embodiment, the carousel 14 has multiple walls disposed radially on the carousel 14 with consecutive opposed walls defining a slot 25 there between. As such, in one aspect, the carousel 14 has an inner periphery through which button 12 can extend and outer periphery in which between the inner and outer periphery the plurality of walls, slots and/or clips are disposed.

Within a cavity defined in carousel 14 the spiral spring 15 is housed to induce rotation of the carousel 14. The carousel's rotational motion, however, is controlled by teeth on button 12 interacting with two rows of staggered teeth on carousel 14. Specifically, a first set of teeth 19 extend radially from an inner periphery of the opening in carousel 14 to operatively engage teeth 21 radially extending from an outer periphery of the button 12. A second set of teeth 20 radially extending from the inner periphery of the opening in the carousel 14 are placed offset, laterally and longitudinally, from that of the first set of teeth 19. The second set of teeth 20 of carousel 14 also operatively engages teeth 21.

Particularly, when the button 12 is not pressed, the teeth 21 of button 12 spaced slightly offset from the first set of teeth 19 of carousel 14 contact each other such that rotational movement of the carousel 14 is restricted. When the button 12 is depressed, the teeth 21 of button 12 releases engagement of the first set of teeth 19 of carousel 14 thereby allowing the carousel 14 to rotate powered by spiral spring 15. The teeth 21 of button 12, however, are now in the rotational path of the second set of teeth 20 of carousel 14. As a result, the rotating carousel 14 halts, when the second set of teeth 20 contacts teeth 21. When pressure is removed from button 12, e.g., the button is released, the displacement means, e.g., compression spring 13, extends forcing button 12 to travel substantially along the dispenser axis back to its original non-actuated position. The teeth 21 of button 12, as a result, disengages from the second set of teeth 20 of carousel 14 such that the carousel 14 rotates but halts once the teeth 21 of button 12 again engages with the first set of teeth 19 of carousel 14, interrupting the rotational path of the first set of teeth 19.

Using a twelve-clip dispenser, as an example, the carousel advances about $\frac{1}{24}^{th}$ of a full rotation when the button 12 is pressed and the teeth 21 on button 12 disengages from the first set of teeth 19 to engage with the second set of teeth 20. With the button 12 being released, the carousel advances about another $\frac{1}{24}^{th}$ of a full rotation as the teeth 21 on button 12 disengages from the second set of teeth 20 to again engage with the first set of teeth 19. Summed up, the carousel advances $\frac{1}{12}^{th}$ of a full rotation, the total angular displacement of thirty degrees, to advance from a slot on the carousel to the next slot on the carousel in the twelve-clip dispenser. Thus, if the slots on the carousel are nearly equally spaced radially around the carousel, the carousel should advance or rotate for each button press and release using the following approximate fraction of a full rotation:

$$\left(\frac{1}{\text{max clips}}\right) * 2,$$

where max clips=the maximum number of clips in the dispenser.

Spacing the slots substantially equally around the carousel should maximize the total number of clips that may be disposed in the dispenser for retrieval. The number of clips and/or slots in the carousel may vary depending on the application or for other reasons unrelated to the maximum number of slots that may be disposed in the carousel.

The maximum number of clips or slots that may be disposed in the carousel is a function of the size of the clips and the size of the dispenser. The larger the clips the less number of clips/slots may be in the carousel if the size, e.g., the diameter, of the dispenser is maintained. As such, increasing the size of the dispenser may increase the total number of clips or slots that can be placed in the carousel depending on the size and positioning of the clips. In one embodiment, the total number of clips/slots in a carousel corresponds to the total number of teeth or projections 21 on button 12, the total number of teeth 19 on carousel 14 or the total number of teeth 20 on carousel 14. However, in one embodiment, a single tooth, protrusion or projection or a number of teeth, protrusions or projections less than the number of the set of teeth on carousel 14 is provided on the button 12 or vice versa which still provides incremental rotational movement of the carousel 14 as the button 12 is actuated. In one aspect, the tooth or teeth 19-21 has a rounded, curved or angled edge. In one embodiment, the button 12 comprises a cylindrical plate or cover from which the square shaft 17 and at least one tooth, projection or protrusion extends and in one aspect with a rounded, curved or angled edge.

In one aspect of the present invention, the rows of teeth on the button 12 and the carousel 14 are reversed. For example, two rows of teeth radially extend from the periphery of the button 12 and one set of teeth radially extend from the carousel 14. The surface area on the outer periphery of the button and the inner periphery of the carousel also govern the total number of clips or slots in the carousel. For example, the total number of teeth that can be disposed on the button and/or carousel to allow incremental rotation of the carousel can limit the maximum number of clips/slots in the carousel.

This incremental rotational movement of the carousel 14 incrementally exposes the clips in the slots 25 of carousel 14 through lid 11. Lid 11 includes a clip window 26 and a clip indicator 27. The clip window 26 operatively exposes a clip in one of the slots 25 of carousel 14 for retrieval. The clip indicator 27 exposes a label 24 on carousel 14, e.g., via a window through the surface of the lid 11, identifying a clip number, e.g., the number of clips remaining in the dispenser or the number of clips that have been dispensed. Therefore, a user does not have to visually distinguish between an empty slot and a clip filled slot or guess or remember the number of clips left in the dispenser and/or the number of clips retrieved.

Additionally, clip window 26 of lid 11, in one embodiment, includes a raised tapered portion extending from the surface of the lid to define a lead-in for a clip applier and in one embodiment is disposed through the surface of the lid. To retrieve a clip from an exposed slot of carousel 14, the jaw members of a clip applier are inserted through clip window 26. The lead-in confines the jaw members to align the jaw members in position over and adjacent to the corresponding legs of the clip in the exposed slot and to reduce splaying of the jaw members to prevent the clip from being dropped once retrieved. Therefore, clip window 26 further guides a clip applier to ease retrieval of a clip from the exposed slot of carousel 14.

In the embodiment shown, the clip window 26 is situated on the lid 11 to expose clip or slot of carousel 14, i.e., provide an opening to access a single clip in the carousel, when the teeth 21 of button 12 engage the first set of teeth 19 of carousel 14. Likewise, the clip indicator 27 is situated on the lid 11 proximate to the clip window 26 to expose the corresponding label 24 for the exposed slot of carousel 14, i.e., provide an opening to view one label on the carousel, when the teeth 21 of button 12 engage the first set of teeth 19 of carousel 14.

In another embodiment, the clip window 26 is situated in an offset position relative to the slots of carousel 14, when the teeth 21 of button 12 engage the first set of teeth 19 of carousel 14. As a result, when the button 12 is not pressed, access to the clips is restricted, i.e., a slot in the carousel is not exposed. Thus, if the dispenser is inadvertently turned upside down or otherwise upset, clips are prevented from falling out through the clip window 26. In this case, to expose a clip, e.g., positioning the clip or slot of carousel 14 below the clip window 26, the button is pushed to cause the teeth 21 of button 12 to engage the second set of teeth 20 of carousel 14 and remains pushed to maintain this engagement and thus exposure of the clip to be retrieved.

Clip window 26 and/or clip indicator 27, in one embodiment, is placed on the side or outer periphery of the lid 11 with the clips/slots 25 and labels 24 on the carousel 14 correspondingly positioned to face out towards the periphery of the lid. In various other embodiments, the clip window 26 and/or clip indicator 27 are provided in various positions, angles and sizes on lid 11 to mirror the various positions, angles and sizes of the clips/slots 25 and labels 24 on the carousel 14. In other words, clip window 26 is so positioned to provide an opening to retrieve a clip from at least one slot 25 of carousel 14 and clip indicator 27 is so positioned to provide an opening to view at least one label 24 on carousel 14.

The size and/or placement of the teeth 21 on button 12 and the first set of teeth 19 and the second set of teeth 20 on carousel 14 govern the incremental rotational movement of carousel 14. The larger the space between teeth 19-21, the greater the rotational movement or angular displacement of carousel 14 occurs or is permitted. Similarly, reducing the width or size of the teeth 19-21 increases the space between teeth 19-21 and thereby allows an increase in rotational movement of carousel 14. The opposite also occurs in that reducing the space between teeth 19-21 or increasing the size of teeth 19-21, reduces the allowable amount of rotational movement or angular displacement of carousel 14.

Equally spacing the teeth 21 on button 12 relative to the teeth 19 and teeth 20 on carousel 14 provides a substantially symmetrical and balanced rotation of the carousel and ensures proper alignment of the clip window 26 over a slot in the carousel 14 to allow access to a clip for retrieval. As such, placing each tooth of the first set of teeth 19 proximate each slot of carousel 14 ensures that rotational movement of the carousel 14 halts near each slot of carousel 14 when teeth 21 of button 12 engage teeth 19. As lid 11 does not move, the clip window 26 is located where the carousel 14 halts and a slot in carousel 14 can be accessed through clip window 26. Likewise, the clip indicator 27 is located where the carousel 14 halts and a label on the carousel 14 can be viewed through clip indicator 27. Therefore, the placement of the first set of teeth 19 relative to the slots 25 of carousel 14 can vary as long as the clip window 26 is so positioned as to provide access to a clip when the carousel 14 is not rotating as teeth 21 of button 12 engages teeth 19.

It should be appreciated that other types of actuators or regulators may be used in combination with or instead of button 12, for example, a lever, a dial, a switch or another type of actuator or regulator capable of moving teeth 21 in/out of engagement of teeth 19 and 20. The teeth 19-21 may also be disposed on separate components such as wheels connected to the button and/or carousel. Also, separate plates, disks or similar components that are coupled to the lid 11 and move with the carousel's rotation can provide labels, openings, slots, covers or windows for the clip windows and/or indicators. Use of separate components may assist in the manufacturing of the dispenser.

Figure 3:
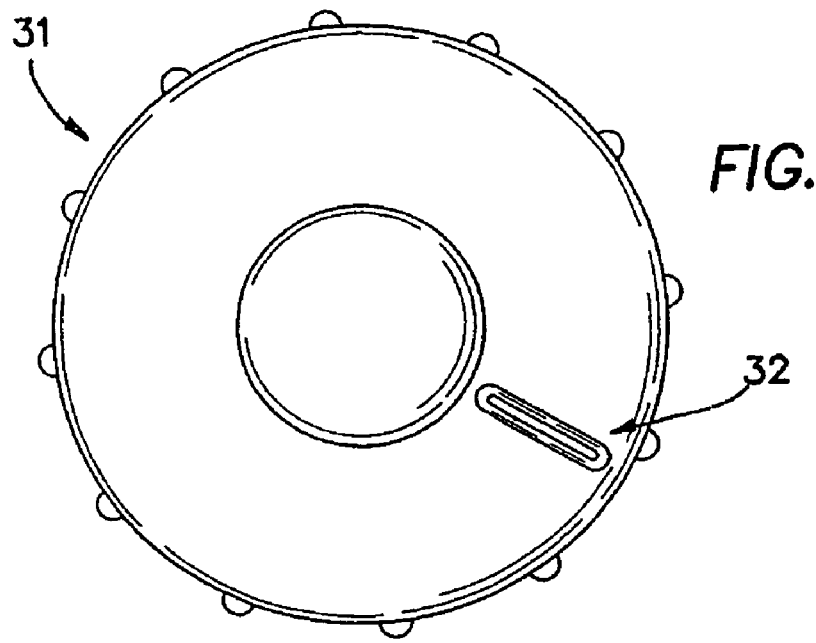
FIG. 3 is a top view of one embodiment of a surgical clip dispenser.

In FIG. 3, another embodiment of a clip dispenser 31 storing numerous surgical clips, e.g., twenty-four clips, is shown. Through clip window 32, a single clip is exposed and accessible through which jaw members of a clip applier (not shown) may be inserted and guided to retrieve the exposed clip. After the clip has been retrieved from the dispenser 31, the dispenser 31 automatically advances to expose another clip. Therefore, clip retrieval is quick, easy and error free. In one aspect, a clip indicator disposed or included in the clip dispenser, e.g., via a window through the surface of the lid, identifies the number of clips dispensed or the number of clips remaining in the dispenser.

Figure 4:
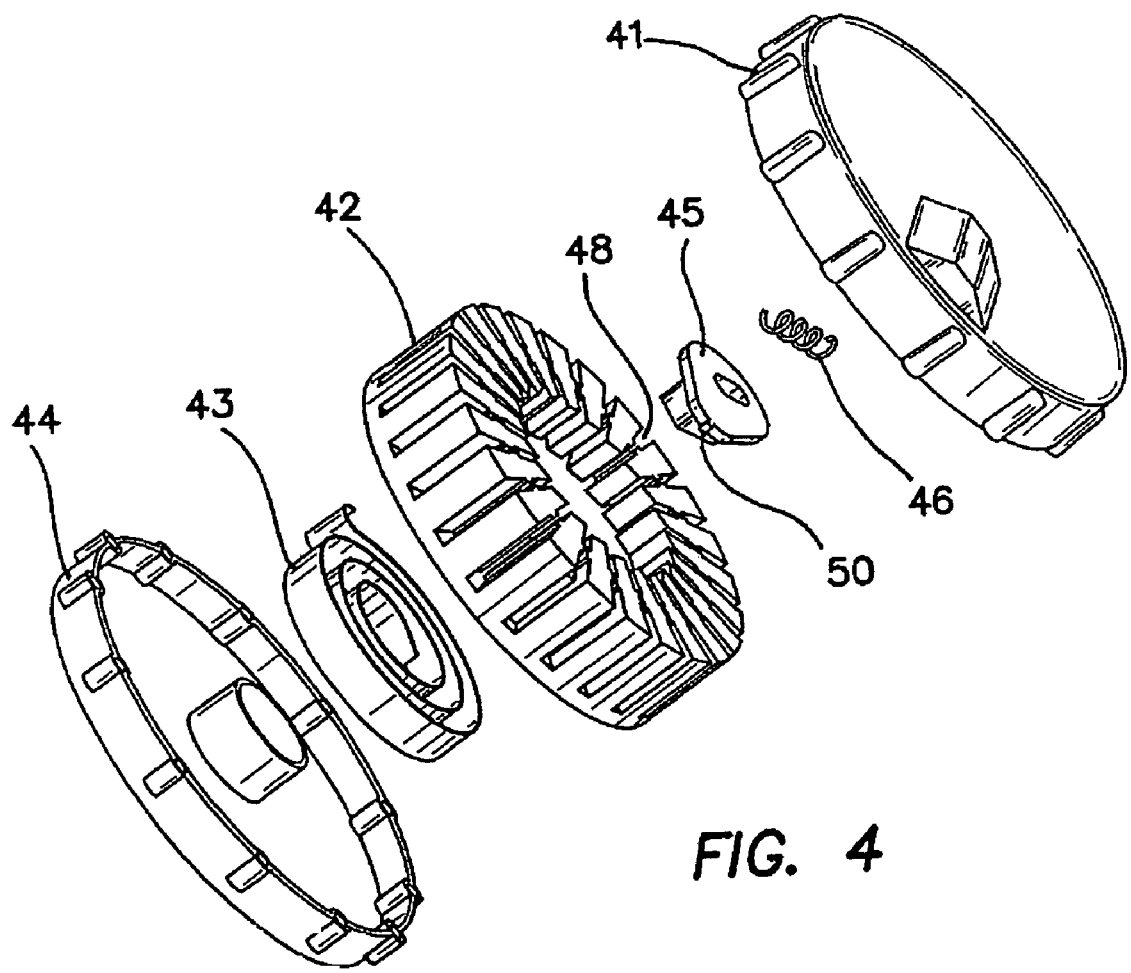
FIG. 4 is an exploded perspective view of one embodiment of a surgical clip dispenser.

Referring now to FIG. 4, one embodiment of a clip dispenser of, for example, FIG. 3 is shown. A lid 41 is connected to a base 44 to define a container for enclosing a carousel 42, a spiral spring 43 and clips disposed in slots 48 in the carousel 42. Clip housing or carousel 42, in one aspect, includes numerous slots 48 disposed radially along the carousel 42. Twenty-four slots are shown, though more or less slots may be provided. In one embodiment, the carousel has multiple walls disposed radially on the carousel with consecutive opposed walls defining a slot there between.

Extending through the middle or opening in carousel 42 is an actuator or regulator, e.g., pawl plate 45. The pawl plate is spring loaded with a spring 46 disposed in a cavity of the pawl plate 45. The spring 46 is angled relative to the center of the pawl plate 45 to induce the pawl plate 45 to move radially and rotationally. In one aspect, the spring 46 is disposed within a cavity of the pawl plate 45. Extending from one end of the pawl plate 45 is a protrusion, projection or tooth 50 and in one embodiment has a rounded, curved or angled edge. The pawl plate 45, in another embodiment, extends to or tapers to a point or tip and in another embodiment is a cylindrical plate having a protrusion, tooth or projection. Pawl plate 45 controls or regulates the rotational movement of carousel 42 powered by spiral spring 43, which in one embodiment induces rotational movement of the carousel 42 along the direction of arrow C (FIG. 5).

In one aspect of the present invention, a square housing, recess, guides or slot disposed in and extending from a cavity formed in base 44 receives a square shaft or cornered shaft extending from the pawl plate 45. The interaction of the base with the shaft, e.g., counteracting means, counteracts excess rotational force applied by the spiral spring 43 through the carousel 42 to prevent additional or unintended rotational movement of the pawl plate 45. In one embodiment, the carousel 42 has an inner periphery through which pawl plate 45 and/or the square shaft can extend and an outer periphery in which between the inner and outer periphery the multiple walls, slots and/or clips are disposed.

Figure 5:
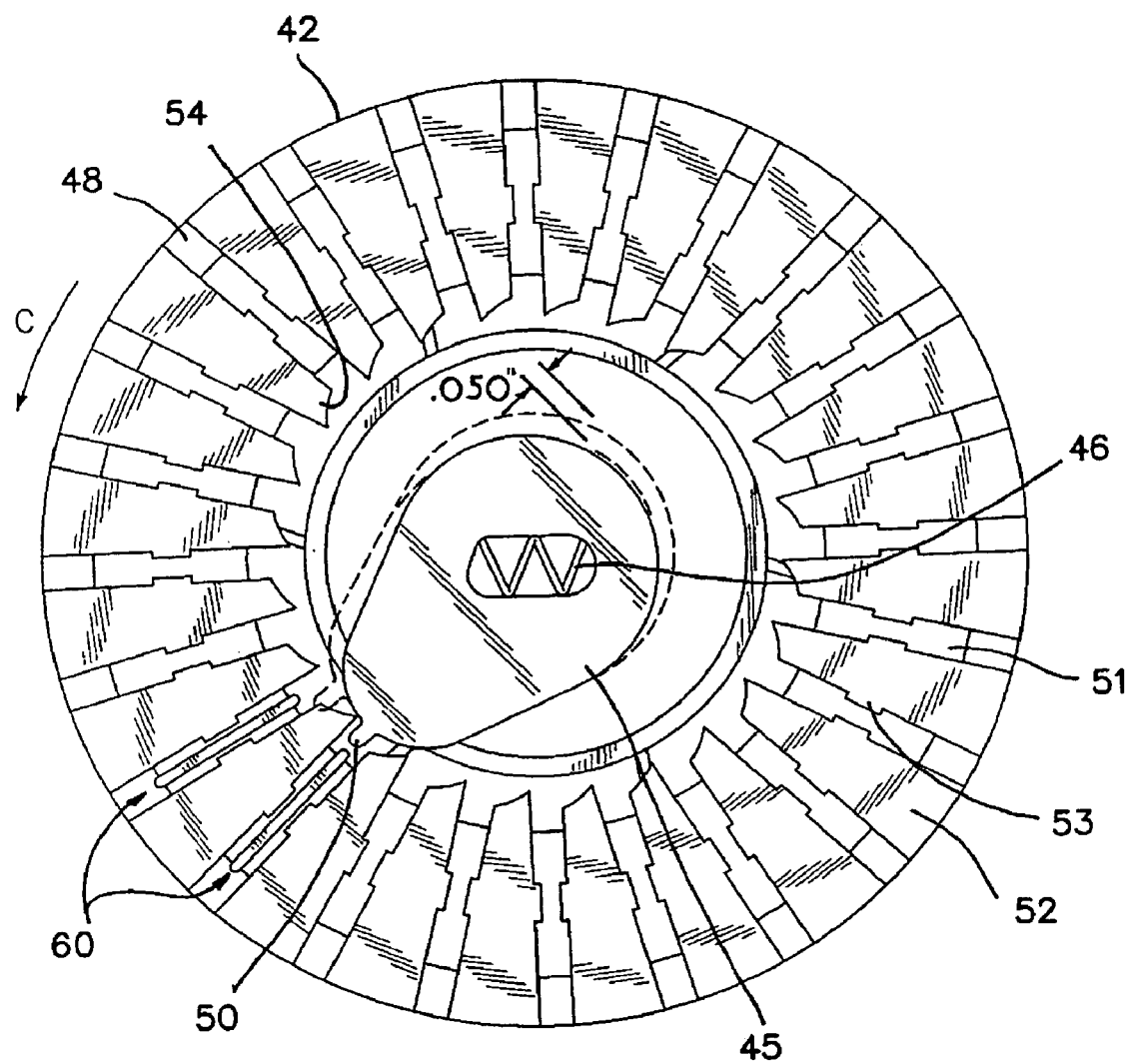
FIGS. 5-8 are top views of embodiments of a surgical clip dispenser in which an actuator and clip housing move relative to each other for clip retrieval.

Referring now also to FIG. 5, when pawl plate 45 or a portion or components included with or integrated with the pawl plate 45, e.g., tip, projection, or tooth 50, is disposed in a slot 48, rotational movement of the carousel 42 is restricted. In other words, the spiral spring 43 induces rotational movement of the carousel 42 in the direction of arrow C while at the same time the pawl plate 45 resists rotational movement and thus the rotational movement of the carousel 42.

When jaw members of a clip applier move towards or are inserted in the slot 48, one of the jaw members 61 contacts or displaces the pawl plate projection or tooth 50 from the slot 48 thereby allowing the carousel 42 to rotate. In particular, the tooth 50 of pawl plate 45 is moved radially inward causing the tooth 50 to be temporarily pushed out of the path of the rotating carousel. Otherwise stated, the tooth 50 clears or loses initial contact of the wall 52, in one aspect the tip or protrusion 54, forming the slot from which the clip was retrieved and which separates the slot from which the clip was retrieved and the next slot from which the next clip is to be received. The resilience and positioning of the spring 46 with the pawl plate 45 allows the pawl plate to move radially inward.

Once or as the projection of the pawl plate clears the wall 52 and the clip and/or jaw members are removed or clears the carousel, the rotational movement is not restricted and as such spiral spring 43 causes the carousel 42 to rotate. The spring 46 also causes pawl plate 45 to slightly rotate or pivot about the base 44 and travel radially towards the carousel to engage or be ready to engage the next slot or wall. In one aspect, the protrusion 54 on the wall 52 is sloped or angled, e.g., an angled portion, to assist the return of the pawl plate projection or tooth back into the path of the carousel to engage the next slot or wall. In one embodiment, after the pawl plate is displaced the tooth 50 clears the wall 52 but is positioned on or adjacent to the protrusion 54 in a ready position ready to engage the next slot and once the carousel 42 rotates the tooth 50 engages the next slot. The pawl plate 45, in one embodiment, contacting the carousel 42, e.g., the next slot or wall, rotates back in the opposite direction, but in the same direction as the rotating carousel 42 to put the pawl plate back to its original resting position. One or more posts, tabs or slots in base 44 limits the rotational movement of the pawl plate to only allow the pawl plate 45 to rotate back to its original position. As a result, the carousel's rotation halts.

In one embodiment, the pawl plate 45 travels towards and away from the carousel 42 for about 0.05 inches and rotates for about six degrees in both the clockwise and counterclockwise directions. A helper spring (not shown), in one aspect, disposed substantially perpendicular to the pawl plate and proximate the tooth 50 urges pawl plate 45 laterally to assist pawl plate 45 into the next slot. In another embodiment, the spring 46 is replaced by at least two springs or resilient components, one to bias the pawl plate radially towards the carousel 42 and another to bias the pawl plate in a rotational direction opposite the rotational direction of the carousel 42.

Using a twenty four-clip dispenser, as an example, the carousel 42 advances about $\frac{1}{24}^{th}$ of a full rotation or 15 degrees when the pawl plate 45 is displaced to advance the slot on the carousel to the next slot on the carousel. Thus, if the slots 48 on the carousel 42 are nearly equally spaced radially around the carousel, the carousel should advance or rotate for clip retrieval when the pawl plate is displaced according to the following approximate fraction of a full rotation:

$$\left(\frac{1}{\text{max clips}}\right),$$

where max clips=the maximum number of clips in the dispenser.

In one embodiment, a fill portion 51 extends in each slot to prevent movement of a clip 60 in the slot towards the center of the carousel 14, 42. The fill portion 51, in one aspect of the present invention, conforms to the shape of the clip 60. For example, fill portion 51 includes a bend in which the apex portion of a clip 60 rests and arms of the clip extend on either sides of the fill portion. Side tabs 53 limit lateral movement of the clips within the slots and align the clips to be retrieved in a substantially straight or upright manner. Sidewalls of the lid 41 or base 44 restrict radial movement of a clip 60 in a slot from the carousel. In one embodiment, one or more slotted walls with slots or openings to receive the projection, protrusion or tooth of the pawl plate, retractable walls or doors or low height walls extending along the entire or portions of the inner periphery of the carousel 14, 42 restrict radial inward movement of a clip 60 towards the pawl plate 45. A jaw member of a clip applier retrieving a clip 60, for example, would displace the retractable wall including pawl plate 45.

Walls 52 of carousel 14, 42 in one embodiment further define each slot 48, cut outs of the carousel 14, 42. Each wall 52 is substantially identical and tapers towards the pawl plate 45 and the center of carousel 42. The tapered end of each wall 52 is angled into an oblique tip or triangle 54. As such, an angled tooth, tip, projection or protrusion is provided proximate each slot 48 of carousel 14, 42.

In one embodiment, the walls 52 are teeth disposed radially around the pawl plate with the space between two consecutive teeth defining a slot. In another embodiment, separate teeth, e.g., a tooth wheel, connected to or integrated with the carousel 14, 42 and adjacent to slots 48 are provided. A center member or fill extending substantially perpendicularly from each tooth and connecting each consecutive tooth may act as the fill portion 51.

Figure 6:
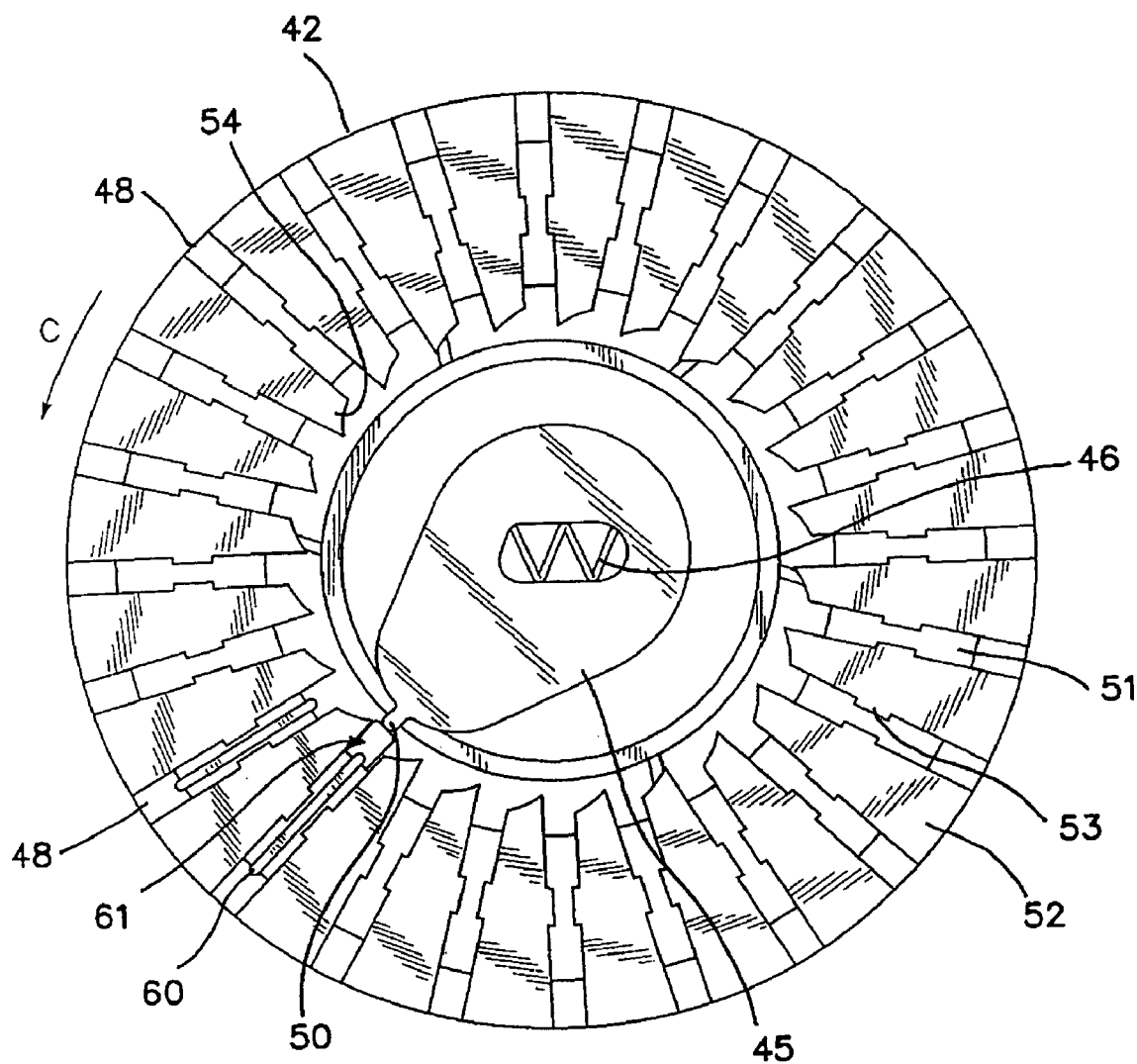
Figure 7:
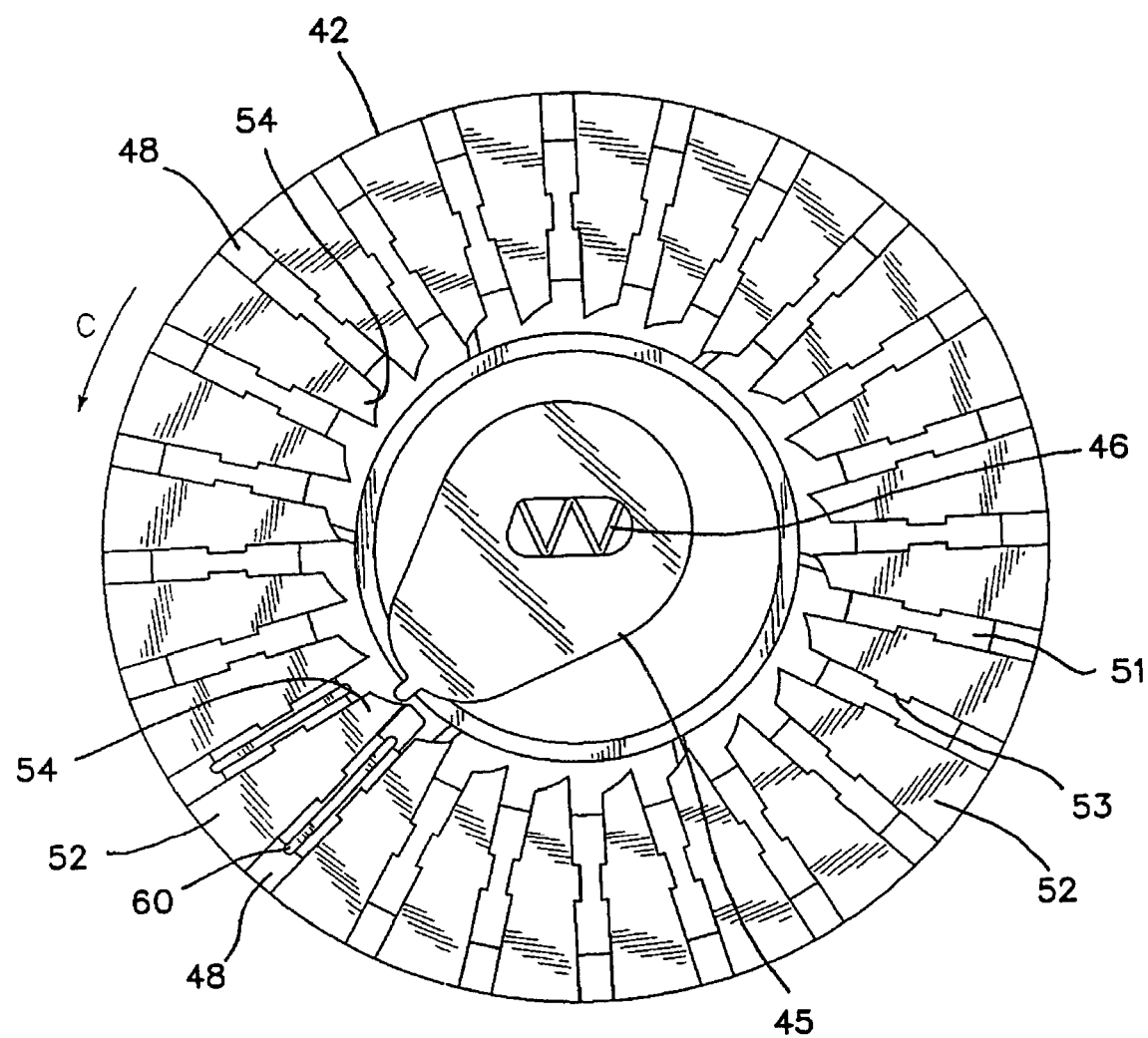
Figure 8:
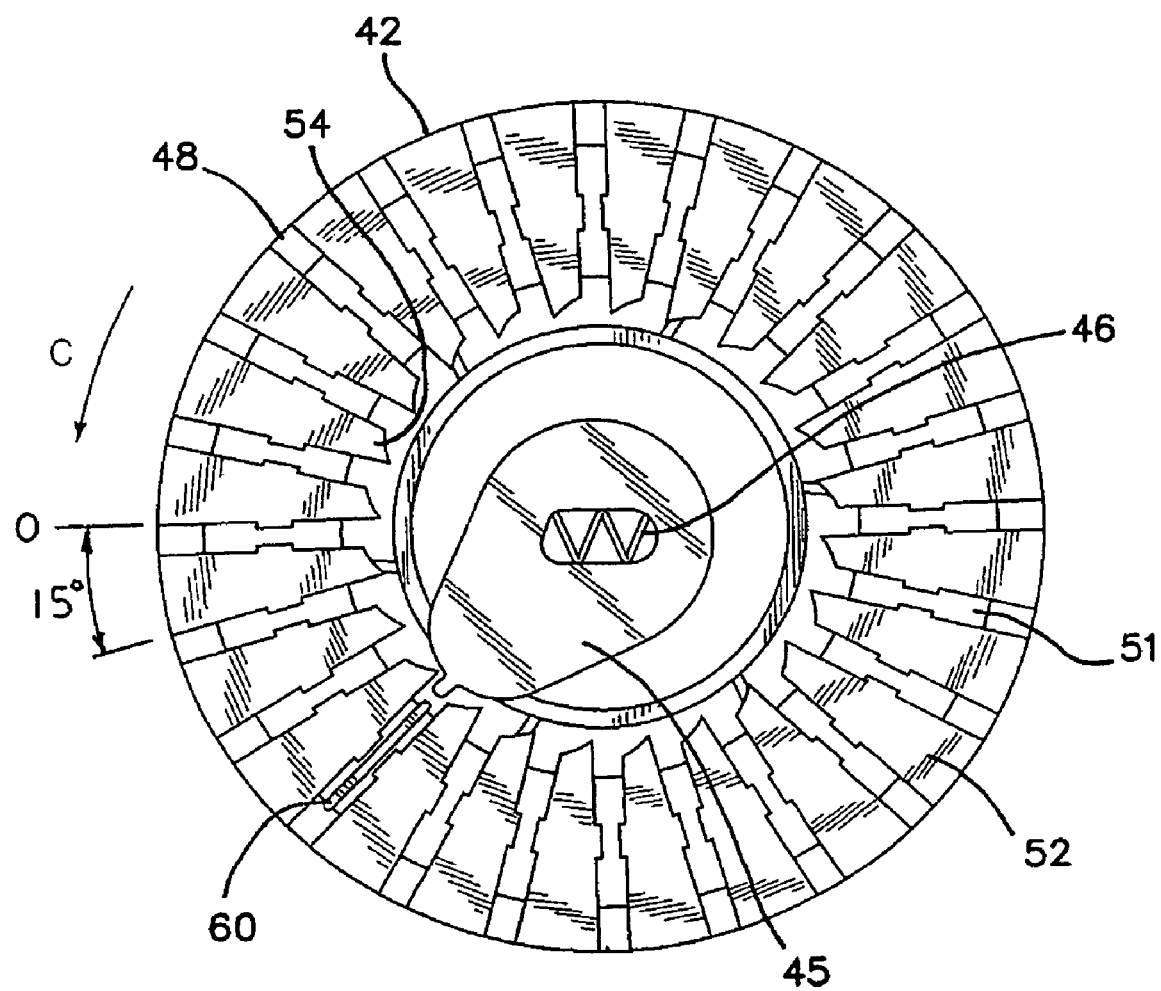

Referring back to the clip retrieval operation previously described and FIGS. 3-8, when a jaw member 61 of a clip applier contacts or displaces the pawl plate 45 from the slot 48, the spring 46 in pawl plate 45 compresses as shown in FIG. 6. Once the displaced pawl plate 45 clears the tip or pinnacle of the oblique triangle end or protrusion 54 of wall 52 and the clip and/or jaw members are removed, the carousel 42 rotates powered by spiral or coil spring 43. The displacement means, e.g., spring 46, is also allowed to extend and rotate the pawl plate 45 and thereby causing the pawl plate 45 to substantially follow the angled or sloped edge of the oblique triangle or protrusion 54 as shown in FIG. 7. In one embodiment, after the pawl plate is displaced the pawl plate 54 clears the wall 52 but is positioned on or adjacent to the protrusion 54 in a ready position ready to engage the next slot and after the carousel 42 rotates, the pawl plate engages the next slot. As the pawl plate 45 engages the next slot 48 or wall 52 further rotation of carousel 42 is restricted as shown in FIG. 8. With the pawl plate 45 being displaced and allowed to slightly rotate prior to the rotation of the carousel, rotation of the carousel 42 to the next slot is ensured.

The incremental rotational movement of the carousel 42 incrementally exposes the clips 60 in the slots 48 of carousel 42 through lid 41. Lid 41 includes a clip window 32 that operatively exposes a clip 60 in one of the slots 48 of carousel 42 for retrieval. The clip window 55 also, in one aspect, defines a lead-in for a clip applier to align and guide jaw members of the clip applier in retrieving the exposed clip and in one embodiment is disposed through the surface of the lid. In one embodiment, a clip indicator (not shown) exposes a label on the carousel 42 to identify a clip number.

Figure 9:
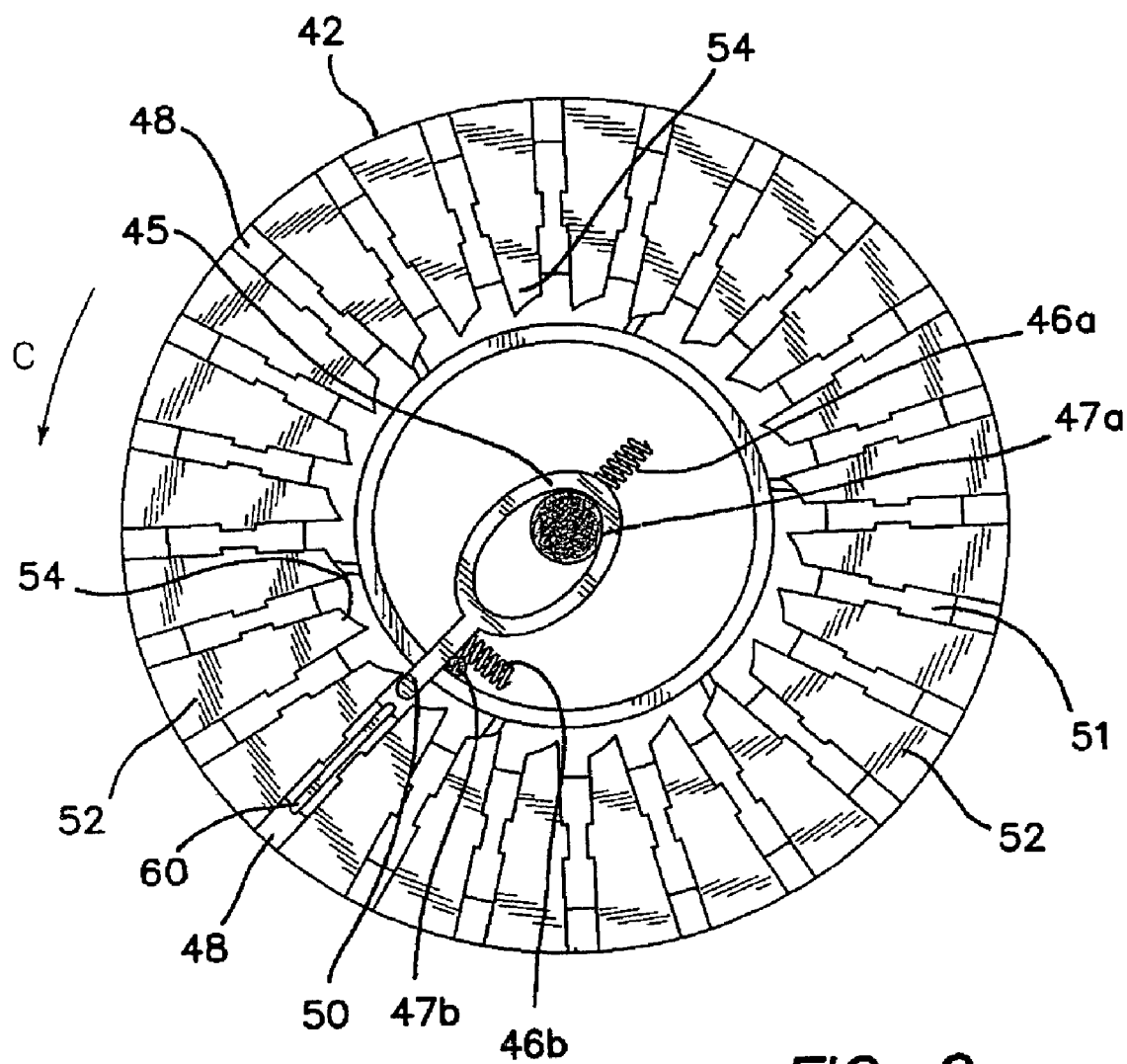
FIG. 9 is a top view of one embodiment of a surgical clip dispenser with another regulator or actuator and a clip housing.

In FIG. 9, when pawl or cylindrical plate or disk 45 or a portion or components included with or integrated with the pawl plate 45, e.g., end, tip, projection, protrusion or tooth 50, is disposed in a slot 48, rotational movement of the carousel 42 is restricted. The contact of the pawl plate with the post 47b prevents rotational or pivotal movement of the pawl plate, which curtails rotational movement of the carousel induced by spiral spring 43. The tooth 50 of pawl plate 45 moved radially inward causes spring 46a to compress and causes the tooth 50 to be temporarily pushed out of the path of the rotating carousel or to clear or lose initial contact of the wall 52, in one aspect the protrusion 54. The resilience and positioning of the spring 46a and post 47a with the pawl plate 45 allows the pawl plate to move radially inward and limits the total amount of radial movement. With the rotational movement of the carousel no longer restricted by the pawl plate 45 and the removal of the clip and/or jaw members, the carousel 42 rotates. The spring 46b also not restricted extends causing the pawl plate 45 to rotate or pivot about post 47a. Likewise, spring 46a extends causing the pawl plate to move radially outward towards the next slot to engage or be ready to engage the next slot. The pawl plate 45 in one embodiment contacting the carousel 42 rotates back in the opposite direction, but in the same direction as the rotating carousel 42 powered by the spiral spring 43, compressing spring 46b, and until the pawl plate 45 contacts the post 47b in which the carousel's rotation halts.

As such, the pawl plate 45 travels radially towards and away from the carousel assisted by compression spring 46a and post 47a disposed through an aperture or cavity in pawl plate 45 or otherwise connected to pawl plate 45. The pawl plate 45 also rotates or pivots in both the clockwise and counter-clockwise directions assisted by a post 47b connected to the base 44 and a compression or helper spring 47b disposed substantially perpendicular to the pawl plate and proximate the tooth 50 to urge pawl plate 45 laterally to assist pawl plate 45 into the next slot.

Figure 10:
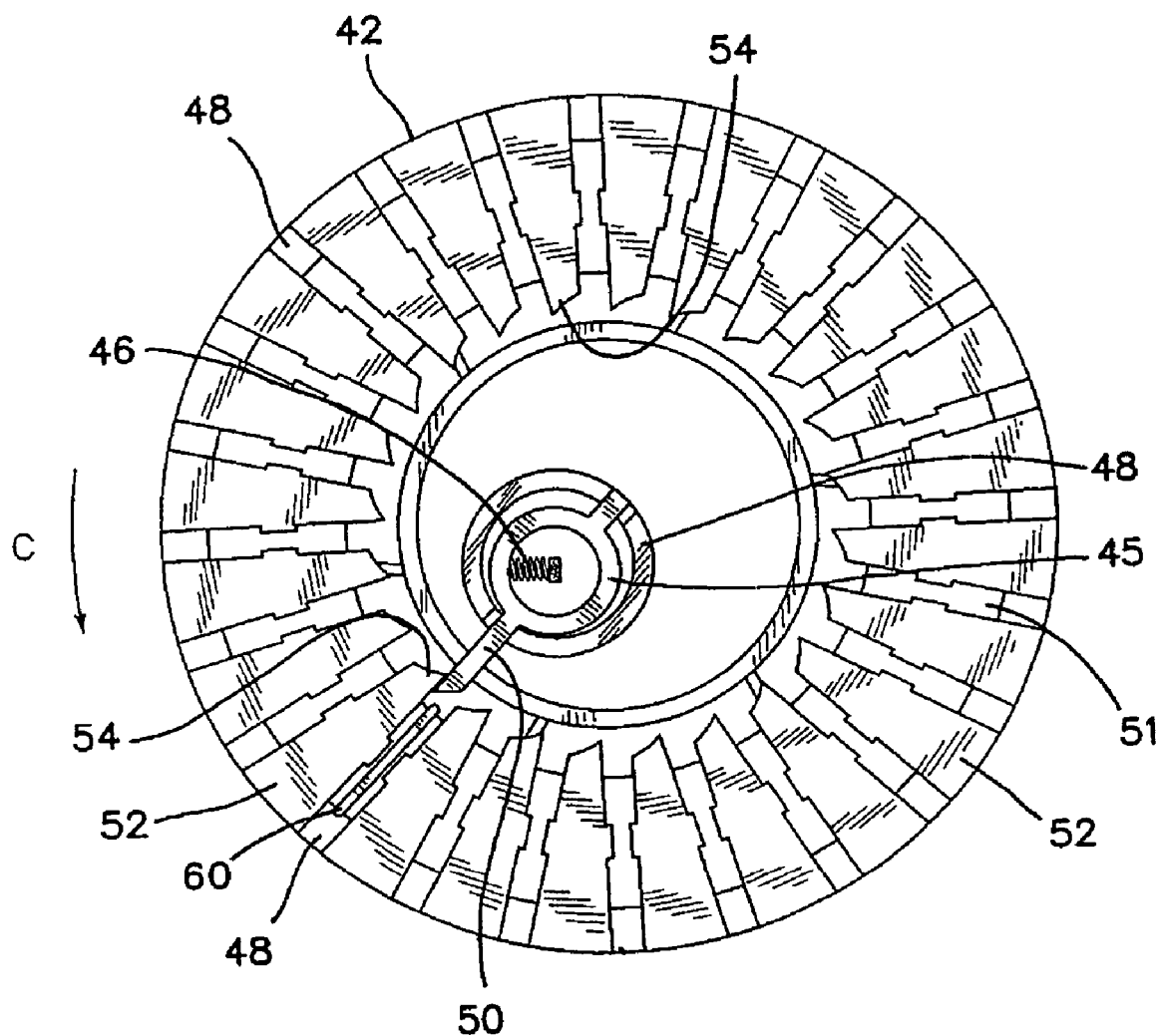
FIG. 10 is a top view of one embodiment of a surgical clip dispenser with another embodiment of a regulator or actuator and a clip housing.

In FIG. 10, the tooth, projection or protrusion 50 of pawl or cylindrical plate or disk 45 disposed in slot 48 restricts rotational movement of the carousel 42 and when it's displaced along with the removal of the clip and/or jaw members from the slot 48 the carousel 42 rotates. Spring 46 permits pawl plate 45 to retract and rotate or pivot within a guide 48 and then extend and travel radially towards the carousel to engage or be ready to engage the next slot. The guide 48 coupled to the base 44 limits the rotational and translational movement of the pawl plate to allow the pawl plate 45 to rotate and extend back to engage or be ready to engage the next slot. As a result, the carousel's rotation halts. In particular, the pawl plate 45 travels towards a slot assisted by compression spring 46 disposed through an aperture or cavity in pawl plate 45 or otherwise connected to pawl plate 45 and the guide 48. The pawl plate 45 also rotates or pivots in the counter-clockwise direction assisted by the compression spring 46. The guide 48 limits the amount of rotational and radial movement of the pawl plate 45. Together the guide 48 and the compression spring 46 ensure that the pawl plate engages the next slot.

As previously mentioned, the spacing of the slots, total number of slots and/or the size of the carousel governs the total number of clips that may be disposed in the dispenser for retrieval. The maximum number of clips or slots that may be disposed in the carousel is also a function of the size of the clips and the size of the dispenser. Additionally, the number of clips and/or slots in the carousel may also vary depending on the application or for other reasons unrelated to the maximum number of slots that may be disposed in the carousel.

In one embodiment, an actuator or regulator comprising a pawl plate with the dispenser provides both or either manual or automatic advancement of the carousel. In other words, movement of the actuator causes the pawl plate to be displaced from the exposed slot, which advances the carousel. As a result, the next slot/clip is exposed. For example, a tab extending from a periphery of a button connected to the pawl plate can be inserted between the clip and pawl plate when the button is pressed to move the pawl plate away from the carousel. When the button is released the carousel is allowed to rotate and the pawl plate engages the next slot halting further advancement of the carousel.

In another embodiment, the pawl plate 45 is allowed to rotate completely around the inner periphery of the carousel 42. The lid 41 is connected to pawl plate 45 to rotate as the pawl plate rotates and is rotatably connected to base 44. A slot is provided in the lid at the pawl plate to lid connection to allow the pawl plate to traverse laterally without causing lateral movement of the lid. The clip window 47 on lid 41 is positioned proximate the tooth 50 of pawl plate 45 and over the exposed slot in carousel 42. As a clip is retrieved, the pawl plate 45 advances to the next slot powered by spring 46. The lid 41 connected to the pawl plate 45 also rotates and thus positions clip window 32 over the next slot.

In this embodiment, the spiral spring 43 may be omitted. An angled tab or a slightly sloped edge, tip, tooth, projection, or protrusion extending from or along a portion of the wall of each slot may be provided to assist in the displacement of the pawl plate from the slot.

In one embodiment, a manual and automatic combination dispenser is provided in which the user accessibility and manipulation of the button type actuator or regulator is incorporated with a pawl plate type regulator. For example, the pawl plate type actuator or regulator is displaced from the slot or moved radially inward by the manipulation or pressing of a button type actuator. In other words, the button type actuator may have multiple protrusions, projections or teeth extending parallel to the dispenser axis that as the button is depressed a tooth engages the tooth of the pawl plate to displace the pawl plate from a slot allowing the pawl plate to rotate and start to engage the next slot. Once the button is released, the carousel rotates and the pawl plate fully engages the next slot for the next clip to be retrieved.

Referring now to FIGS. 1-8, in another embodiment, a clip tab (not shown) extending partially across clip window 26 or clip window 32 or a swing plate pivotally (not shown) connected to the lid restricts movement of the exposed clip. Thus, if the dispenser is inadvertently turned upside down or otherwise upset, clips are prevented from falling out through the clip window. The clip tab covers an apex portion of the clip and thus permits jaw members to engage the arms of the exposed clip. The retrieval of the clip causes the apex to contact the clip tab, which gives way or otherwise retracts to permit retrieval of the clip. The clip window may be provided in various positions, angles and sizes to mirror and thereby provide access to the respective various positions, angles and sizes of the clips/slots in the carousel.

In one embodiment, a button stop is provided that prevents button actuation until the clip exposed in the clip window is retrieved or after the last clip in the dispenser has been retrieved. For example, in one aspect, a spring-loaded lever disposed in a clip slot that is used to push the engaging teeth or tooth out of the slot to allow continued rotation is dislodged or activated by the removal of the clip. Other embodiments include a tooth (the last tooth) that extends the length of the inner periphery of the carousel 14, 42 or a last tooth is a L-shaped tooth on carousel 14, 42 that restricts travel of button towards base 16 or returning after being depressed to prevent further actuation of button 12 once the last clip slot is reached or the last clip has been dispensed.

In various embodiments, the spiral or coil spring 15, 43 is arranged to allow a single full rotation or predetermined portion of a rotation of the carousel 14, 42. For example, the spiral spring is wound or coiled within a cavity in the carousel to power or tighten the spring that when the carousel's rotational path is not inhibited, the spring is released, e.g., unwound or loosen. Thus, with each incremental rotation of the carousel the spring unwinds. At the stop position, e.g., the last clip is dispensed or exposed or a full or predetermined portion of a full rotation or revolution is achieved, the spring is unwound or unable to induce further rotational movement of the carousel. Therefore, the spiral spring, biasing means or other similar types of components able to induce rotational movement of the carousel is arranged to power or induce rotational movement of the carousel for a predetermined or limited revolution before stopping or losing power and thereby preventing further access to the slots/clips or dispensing of clips.

In another aspect of the present invention, the clip dispenser may be made with less bulky and lighter components than metal components and may also be disposable. For example, the embodiments of the present invention can be implemented by incorporating molded plastic parts and/or be attached to a user's wrist. In one aspect of the present invention, the clip dispenser may be inserted into a patient through a hand access port or another opening to position the clip dispenser proximate a clip applier that's inserted into a patient through the same or another access port such as a trocar or a hand access port. The clip dispenser of the present invention by ensuring operational ease and accuracy of dispensing and retrieval of the clips allows such an operational procedure.

Accordingly, the present invention provides a surgical clip dispenser and clip dispensing methods thereof. Although this invention has been described in certain specific embodiments, many additional modifications and variations would be apparent to those skilled in the art. It is therefore to be understood that this invention may be practiced otherwise than specifically described, including various changes in the size, shape and materials, e.g., the button, pawl plate, shaft, carousel, window, base, lid, carousel, springs, indicators, etc., without departing from the scope and spirit of the present invention. Thus, embodiments of the present invention should be considered in all respects as illustrative and not restrictive, the scope of the present invention to be determined by the appended claims and their equivalents rather than the foregoing description.

The invention claimed is:

1. A surgical clip dispenser holding and dispensing a plurality of surgical clips for retrieval by a clip applier, the dispenser comprising:
    a clip housing having a plurality of walls with consecutive opposed walls defining a slot arranged to hold a surgical clip of the plurality of surgical clips;
    a spring inducing rotational movement on the clip housing; and
    a regulator substantially encompassed by the clip housing, the regulator having at least one projection operationally engaged with a portion of the clip housing, the regulator movable between a first position preventing movement of the clip housing and a second position permitting movement of the clip housing.

2. The dispenser of claim 1 wherein the clip housing is substantially circular with an inner periphery and an outer periphery and comprising a plurality of alternating offset teeth disposed along the inner periphery of the clip housing.

3. The dispenser of claim 2 wherein the plurality of alternating offset teeth of the clip housing further comprises a first set of teeth and a second set of teeth, the first set of teeth positioned vertically and horizontally offset from the second set of teeth on the clip housing and the regulator is substantially disposed within the inner periphery and the at least one projection of the regulator engages the first set of teeth when the regulator is in the first position and the at least one projection of the regulator engages the second set of teeth when the regulator is in the second position.

4. The dispenser of claim 1 wherein clip housing is arranged to rotate about an axis of rotation and the regulator is arranged to traverse along the axis of rotation.

5. The dispenser of claim 1 wherein the regulator comprises a square shaft coupled to the clip housing.

6. The dispenser of claim 1 wherein the regulator in the first position extends and in the second position retracts.

7. The dispenser of claim 1 wherein the plurality of walls further comprises an angular portion extending from each wall operationally engaged with the at least one projection.

8. The dispenser of claim 7 further comprising a spring coupled to the regulator and arranged to permit the regulator to extend beyond the angular portion of each wall and over the angled portion of each wall.

9. The dispenser of claim 1 further comprising a spring coupled to the regulator arranged to induce lateral and rotational movement of the regulator.

10. The dispenser of claim 9 wherein the spring is disposed within the regulator lengthwise along a plane traverse to a plane the at least one projection extends.

11. The dispenser of claim 1 wherein the clip housing further comprises a cavity and the spring is a spiral spring in which the spring is disposed.

12. The dispenser of claim 1 further comprising a lid coupled to the clip housing and having a window sized to expose at least one of the plurality of surgical clips.

13. The dispenser of claim 1 further comprising a lid comprising an indicator identifying the number of surgical clips in the clip housing.

14. The dispenser of claim 1 wherein the at least one projection comprises a plurality of projections radially extending from the regulator, a total number of the plurality of projections corresponding to about half a total number plurality of walls of the clip housing.

15. A surgical clip dispenser holding and dispensing a plurality of surgical clips for retrieval by a clip applier, the dispenser comprising:
holder means storing a plurality of surgical clips;
bias means inducing rotational movement of the holder means; and
resilient means permitting the holder means to rotate for a predetermined angular rotation in a first position and for preventing rotational movement of the holder means in a second position.

16. The dispenser of claim 15 further comprising means for counteracting the induced rotational movement coupled to the resilient means.

17. The dispenser of claim 15 further comprising displacement means inducing one of rotational and lateral movement of the resilient means and vertical movement of the resilient means.

18. A clip dispenser holding and dispensing a plurality of surgical clips for retrieval by a clip applier, the clip dispenser comprising:
a carousel having an outer periphery, an inner periphery, and a plurality of walls disposed radially on the carousel with each consecutive opposed wall defining a slot adapted to holding a surgical clip and a plurality of protrusions proximate each wall disposed along the inner periphery;
an actuator substantially surrounded by the carousel within the inner periphery of the carousel and having at least one tooth extending from a periphery of the actuator operatively engaging at least one of the plurality of protrusions;
a spiral spring connected to the carousel between the inner periphery and the outer periphery to induce rotational movement;
a spring connected to the actuator;
a base connected to the carousel and the spiral spring; and
a lid connected to the base and including a surface having a window disposed there through and having raised portions extending from the surface of the lid.

19. The dispenser of claim 18 further comprising a tab laterally extending from each of the plurality of walls and wherein the surface further comprises a second window disposed there through and the carousel having a plurality of labels located adjacent the plurality of walls.

20. The dispenser of claim 18 wherein the actuator further comprises a generally cylindrical plate from which the at least one tooth extends and a square shaft extending from the plate.

* * * * *